US011561187B2

United States Patent
Ashish et al.

(10) Patent No.: US 11,561,187 B2
(45) Date of Patent: Jan. 24, 2023

(54) NON-INVASIVE AND REMOTE METHOD TO SCREEN CANCER

(71) Applicant: Council of Scientific and Industrial Research, New Delhi (IN)

(72) Inventors: Ashish, Chandigarh (IN); Amin Sagar, Chandigarh (IN); Maulik Dinesh Badmalia, Chandigarh (IN); Kanika Dhiman, Chandigarh (IN); Shiv Pratap Singh Yadav, Chandigarh (IN)

(73) Assignee: Council of Scientific and Industrial Research

( * ) Notice: Subject to any disclaimer, the term of this patent is extended or adjusted under 35 U.S.C. 154(b) by 73 days.

(21) Appl. No.: 16/958,851

(22) PCT Filed: Mar. 25, 2019

(86) PCT No.: PCT/IN2019/050237
§ 371 (c)(1),
(2) Date: Jun. 29, 2020

(87) PCT Pub. No.: WO2019/186577
PCT Pub. Date: Oct. 3, 2019

(65) Prior Publication Data
US 2021/0072169 A1    Mar. 11, 2021

(30) Foreign Application Priority Data
Mar. 27, 2018 (IN) .............................. 201811011202

(51) Int. Cl.
*G01N 23/201* (2018.01)
*G01N 33/483* (2006.01)

(52) U.S. Cl.
CPC ....... *G01N 23/201* (2013.01); *G01N 33/4833* (2013.01); *G01N 2223/054* (2013.01);
(Continued)

(58) Field of Classification Search
CPC ..... G01N 2223/054; G01N 2223/1016; G01N 2223/612; G01N 23/201; G01N 33/4833
See application file for complete search history.

(56) References Cited

U.S. PATENT DOCUMENTS

2007/0258561 A1* 11/2007 Chikawa .............. G01N 23/223
378/45
2009/0299642 A1* 12/2009 French ................ G01N 23/2055
702/19
(Continued)

FOREIGN PATENT DOCUMENTS

EP          1777518 A1    4/2007
WO      WO0034774 A1    6/2000
(Continued)

OTHER PUBLICATIONS

Chikawa, J., Y. Mouri, et al. (2014). "A correlation of breast cancer and calcium levels in hair analyzed by X-ray fluorescence." J Xray Sci Technol 22(5): 587-603.
(Continued)

*Primary Examiner* — Dani Fox
*Assistant Examiner* — Soorena Kefayati
(74) *Attorney, Agent, or Firm* — Belles Katz LLC

(57) ABSTRACT

An in vitro method for detecting presence of cancer includes obtaining a single hair sample. An x-ray beam is emitted from a source towards the hair sample. A small angle X-ray scattering (SAXS) intensity profile is generated after the x-ray beam hits the hair sample. The SAXS profile is received on a detector to obtain SAXS data, which is desmeared and Kratky Analysis is performed. A relative estimation of peak area under 1.38 $nm^{-1}$ to 0.89 $nm^{-1}$ from keratin and lipid content in the hair sample is performed to obtain R and is corrected by dividing by D, thickness of the hair. R' is computed using formula: $10 \times R^2/(D-R)$. The value of R' is compared with clinically validated samples. If R'
(Continued)

Figure 1:
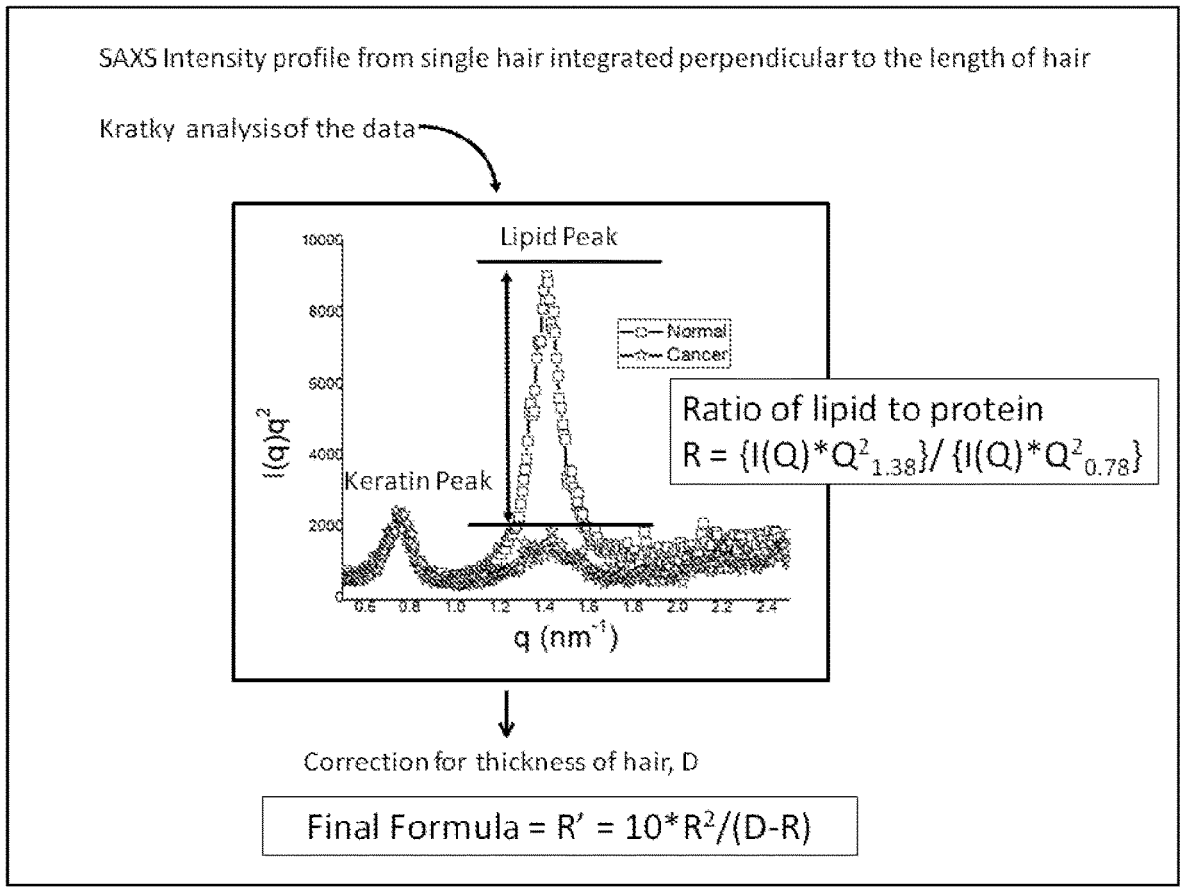

value is below 0.7, it indicates the presence of cancer and if it is above 0.8, it indicates absence of cancer.

3 Claims, 4 Drawing Sheets

(52) U.S. Cl.
CPC ............... *G01N 2223/1016* (2013.01); *G01N 2223/612* (2013.01)

(56) References Cited

U.S. PATENT DOCUMENTS

| | | | | |
|---|---|---|---|---|
| 2009/0325303 | A1* | 12/2009 | Corino | G01N 23/20 436/86 |
| 2010/0135461 | A1* | 6/2010 | James | A61B 6/483 378/70 |
| 2012/0091333 | A1* | 4/2012 | French | G01N 33/92 250/282 |
| 2013/0182824 | A1* | 7/2013 | French | G01N 23/20025 378/79 |
| 2013/0329858 | A1* | 12/2013 | Jiang | G01N 23/201 378/87 |
| 2017/0115240 | A1* | 4/2017 | Herron | G01N 33/4833 |

FOREIGN PATENT DOCUMENTS

| | | |
|---|---|---|
| WO | WO2008000020 A1 | 1/2008 |
| WO | WO2008134800 A1 | 11/2008 |
| WO | WO2010141998 A1 | 12/2010 |
| WO | WO2011000020 A1 | 1/2011 |
| WO | WO2013184999 A1 | 12/2013 |
| WO | WO2018096557 A1 | 5/2018 |

OTHER PUBLICATIONS

Corino, G. L. and P. W. French (2008). "Diagnosis of breast cancer by X-ray diffraction of hair." Int J Cancer 122(4): 847-856.

P.W.French., Dharmica A.H. Mistry, et al. (2012). "Identification of breast cancer associated lipids in scalp hair." Breast Cancer (Auckl). 06, 113-123.

Corino, G. L., P. W. French, et al. (2009). "Characterization of a Test for Invasive Breast Cancer Using X-ray Diffraction of Hair-Results of a Clinical Trial." Breast Cancer (Auckl) 3: 83-90.

P.W.French., Dharmica A.H. Mistry, (2016). "Circulating phospholipids as biomarkers of breast cancer: A review" Breast Cancer (Auckl). 10, 191-196.

Kajiura, Y., S. Watanabe, et al. (2006). "Structural analysis of human hair single fibres by scanning microbeam SAXS." J Struct Biol 155(3): 438-444.

Meyer, P., R. Goergl, et al. (2000). "Breast cancer screening using small-angle X-ray scattering analysis of human hair." J Natl Cancer Inst 92(13): 1092-1093.

Stephenson, J. (1999). "X-ray analysis of hair reveals breast cancer." JAMA 281(17): 1578-1579.

James VI, Corino G, et al. (2005). "Early diagnosis of breast cancer by hair diffraction." Int J Cancer. 10;114(6):969-72.

James VI, (2013). "A Review of Low Angle Fibre Diffraction in the Diagnosis of Disease". British Journal of Medicine and Medical Research, 2231-0614(3).

James VI, Kirby N. (2010). "The connection between the Presence of Melanoma and changes in fibre diffraction patterns". Cancers (Basel), 1155-65(2).

James VI, (2003). "False-Positive Results in studies of changes in fibre diffraction of Hair from patients with breast cancer may not be false". JNCI, 95(2), 170-171.

James VJ, Ford JMO, Buttigieg J (2015) "Then there were none!". Integr Cancer Sci Therap. 10(2).15761.

James VI, et al. (1999). "Using hair to screen for breast cancer." Nature. 398, 33-34.

James VI, (2014). "Using Physics to Diagnose Cancer". Biophys. Rev. Lett., 09, 205.

PCT International Search Report and Written Opinion issued by the International Bureau for PCT Application No. PCT/IN2019/050237, dated Jul. 11, 2019, pp. 1-9.

* cited by examiner

NON-INVASIVE AND REMOTE METHOD TO SCREEN CANCER

CROSS-REFERENCE TO RELATED PATENT APPLICATIONS

The present application is a U.S. national stage application under 35 U.S.C. § 371 of PCT Application No. PCT/IN2019/050237, filed Mar. 25, 2019, which claims priority to Indian Application No. 201811011202, filed Mar. 27, 2018, the entireties of which are incorporated herein by reference.

FIELD OF THE INVENTION

The present invention relates to an in vitro method for detecting cancer using a hair sample. More particularly, the present application is primarily directed to utilizing a non-invasive collection technique and a method for detection and screening for positive identification of malignant cells.

BACKGROUND OF THE INVENTION

There are a number of prior art methods and apparatuses which are used in the detection and treatment of cancer. Fluorescent markers have been used to help identify cancerous tissue within a patient. Radio tracers or markers have also been used in the detection and treatment of cancer. There are also a number of prior art methods and apparatuses which relate to flow cytometry and the act of segregating and counting malignant cells within a tissue sample.

A variety of research to date has indicated the presence of abnormal changes in components of keratin samples, such as hair, taken from subjects, who are afflicted with a pathological state which can include cancer.

X-ray diffraction analysis has shown that subjects with a plurality of certain types of cancers (colon, breast and prostate) and other pathological states (Alzheimer's disease) produce hair samples that have abnormalities in them. The abnormalities are detectable using X-ray diffraction techniques and are consistent with the presence of the pathological state itself.

WO2000034774A1 (James et al.) describes a method for detecting the presence of a gene responsible for causing cancer by exposing at least one hair from the patient to X-ray diffraction and detecting the changes in the ultrastructure of the hair.

WO2008000020A1 (Corino et al.) describes a method for detecting the presence of an abnormal component in a keratin sample taken from a subject suffering from a known pathological state.

US20090299642A1 (French et al.) describes a method of analyzing a keratin sample from a subject for improving sensitivity and specificity of a diagnostic test for a pathological state in the subject.

Meyer et al. (2000), Journal of the National Cancer Institute 92(13), describes a methodology for breast cancer screening using small-angle X-ray scattering analysis of human hair.

Laaziri et al. (2002), Physics in Medicine and Biology 21(47), provides a study to determine whether there is any correlation between the structure of hair and breast cancer or BRC A1/2 mutations.

However, most of the cancer screening and diagnostic techniques available in the art suffer from many limitations, such as:

1) The results cannot be termed as early stage prognosis, screen or diagnostic.
2) Sample collection and processing requires skilled manpower.
3) The techniques involve samples and methodologies prone to cross-contamination.
4) The techniques involve samples and methodologies which require meticulous and extended sample processing.
5) Most importantly, the technique employs methodologies where samples perish and cannot be re-analyzed.
6) Interpretation of the results obtained after screening or analysis require intervention of skilled manpower or manual curation of the data acquired or customized analysis which affects the outcome interpretation.

Therefore, there is a need in the art for providing a non-invasive, reliable, and cost-effective method to screen for presence or absence of cancer.

BRIEF DESCRIPTION OF ACCOMPANYING DRAWINGS

FIG. 1: Flow chart of the SAXS data processing steps and formula which allows analysis of lipid to keratin architecture inside hair corrected for the thickness of hair.

Figure 2:
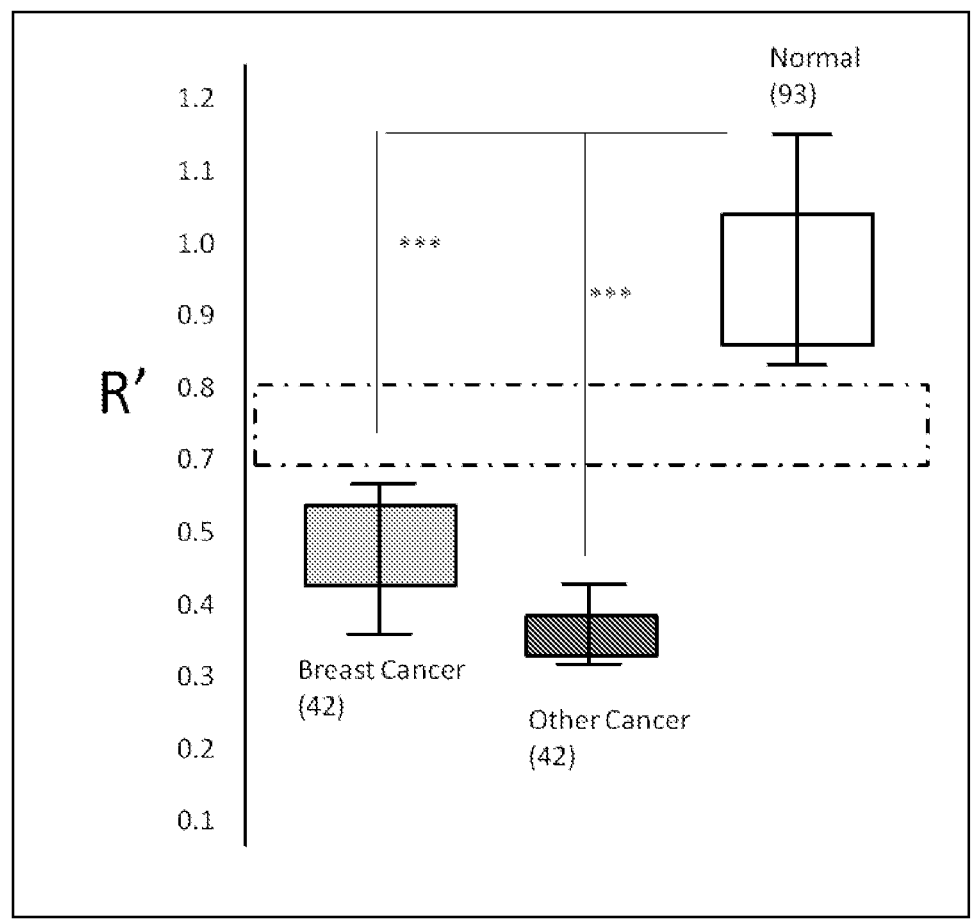

FIG. 2: Box chart representation of the computed R' value from hairs of 42, 42 and 93 cases having orthogonally confirmed profile of having breast cancer, cancers other than breast cancer (e.g. lung cancer, pancreatic cancer, head-and-neck cancer, cervical cancer etc.) and not having any cancer, respectively.

Figure 3:
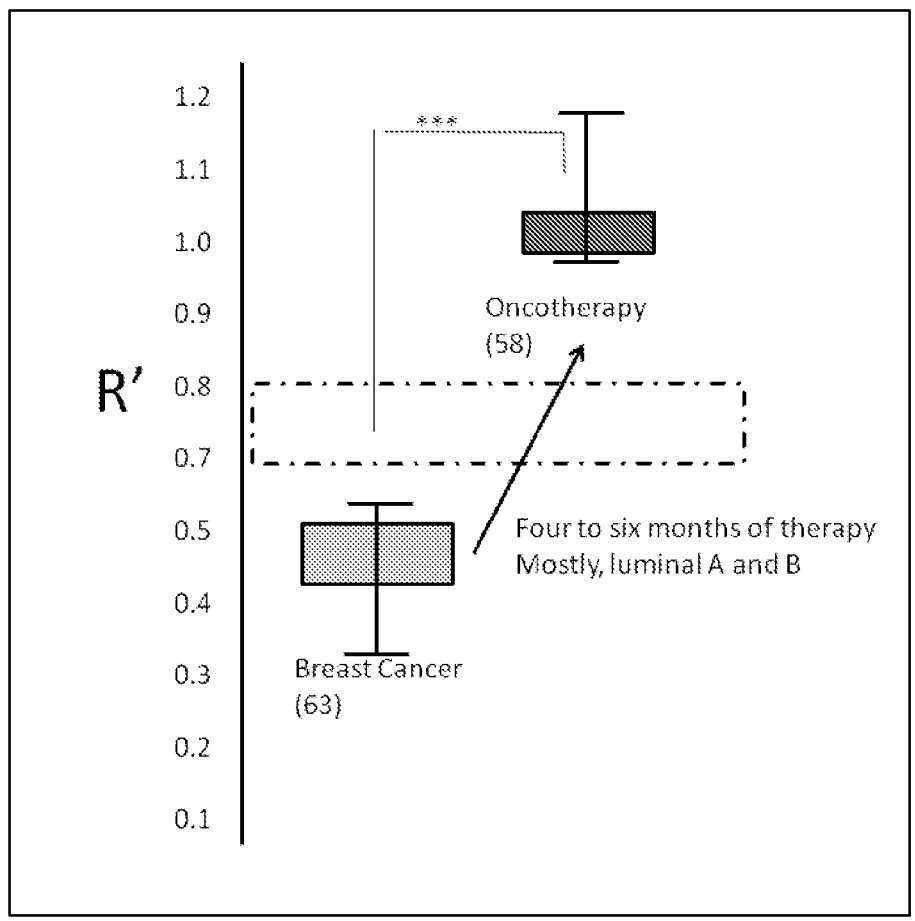

FIG. 3: Box chart representation showing change in R' value as a result of oncotherapy by following 58 of 63 breast cancer patients is presented here.

Figure 4:
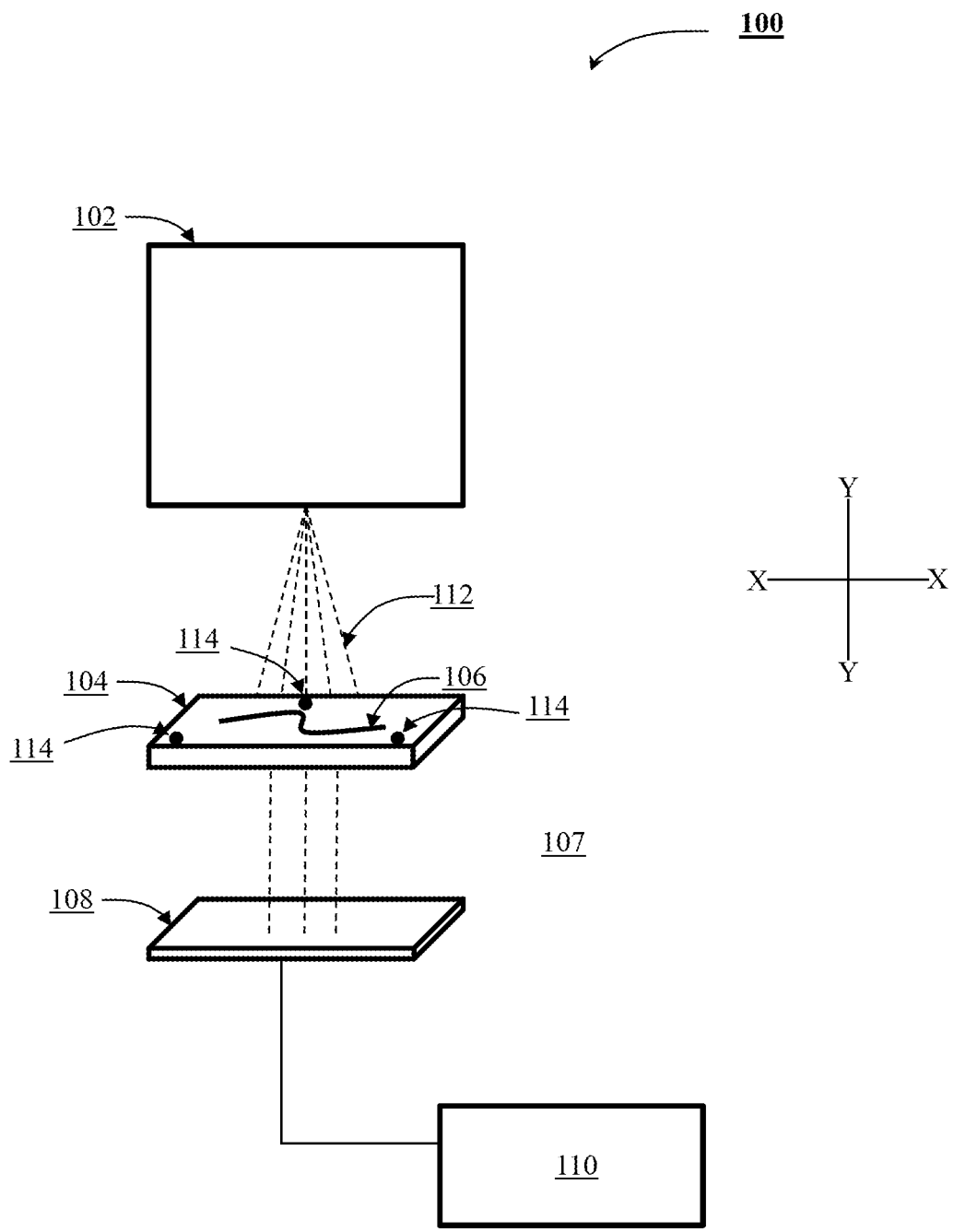

FIG. 4 illustrates a SAXS machine detecting presence of cancer.

FIG. 4 describes an SAXS machine 100. Line collimation x-ray 102 generates x-rays. Hair sample 106 is aligned using a cross-talking hair holder 104 which can move up and down vertically. Pin diodes 114 help in automatically aligning the hair sample 106 in the x-ray beam 112. SAXS data 107 is collected on a perpendicular line detector 108 of x-rays. SAXS data is corrected for beam position, and the SAXS intensity profile was analyzed using a SAXS data processor 110.

OBJECT OF THE INVENTION

The main object of the present invention is to provide a non-invasive and remote hair SAXS based automated screening method for presence or absence of cancer in sample provider.

SUMMARY OF THE INVENTION

Accordingly the present invention relates to an in vitro method for detecting cancer using a hair sample.

In an embodiment of the present invention it provides an in vitro method for detecting presence of cancer, said method comprising the steps of:
(a) obtaining a single hair sample;
(b) generating small angle X-ray scattering intensity profile based on the hair sample to obtain SAXS data;
(c) desmearing the SAXS data and performing Kratky Analysis;

(d) performing relative estimation of peak area under 1.38 nm$^{-1}$ to 0.89 nm$^{-1}$ from keratin and lipid content in the hair sample to obtain R;

(e) correcting value of R of step (d) by diving by hair thickness, 'D' in micron;

(f) using 'D' from step (e), compute R' by the formula: 10×R$^2$/(D−R); and (g) comparing the value of R' with clinically validated samples;

wherein R' value below 0.7 is indicative of presence of cancer and R' value above 0.8 indicates absence of cancer.

In an embodiment of the present invention it provides an in-vitro method wherein small angle X-ray scattering intensity profile is obtained with source of monodisperse X-rays.

In an embodiment of the present invention it provides an in-vitro method wherein the SAXS data in step (b) is collected on detector of X-rays selected from the group consisting of X-ray sensitive films, CCD, 1D, and 2D detector.

In an embodiment of the present invention it provides an in-vitro method wherein the method is used in monitoring the progress or response of patients to different anti-cancer therapies as a function of time and/or medication.

DETAILED DESCRIPTION OF THE INVENTION

The present application provides a method to screen for cancer which overcomes the problem of reliably diagnosing presence of cancer with no stress to the patient, low cost and quick turn-around time of diagnosis. The inventive steps of the present application include formula and programs for: 1) automated SAXS data processing from hair and 2) analysis of presence/absence of cancer in the sample provider.

Overcoming the limitations of the prior art, the Applicant developed a methodology whereby based on analyzing SAXS data from hair samples one can interpret presence/absence of cancer in hair sample provider. It has been described in the prior art that with the onset of cancerous growth, factors secreted by tumors (which traverse through blood to reach hair follicles) leads to altered spatial incorporation of lipid bilayer in hair cells. The differential incorporation of lipids as crystalline or amorphous in hairs from patients lacking or having cancer, respectively can be easily read-out in the SAXS profiles from hair. Previous attempts at such a technology have been based on manual analysis of images. Such technologies lack the ability to be compared with self or others. Furthermore, previous experiments have been done using synchrotron sources of SAXS optics with point collimation, which substantially reduces the application: One, due to non availability of many synchrotron sources for hair scattering, and Two, point collimation limits data collection to a single point in hair which may be malformed or affected in the whole sample. Contrarily, the present methodology acquires SAXS data from: one, a SAXS machine (100) which runs on sealed tube source or is in-house, and two, a stretch of about 3 cm of hair sample (106) which provides a more conclusive information about the inner structure of hair over a period of three months of patient's health status and overcomes any local deformity in the hair due to extrinsic factors during sample abstraction or otherwise. The SAXS optics used the invention, specifically line collimation X-ray (102) coupled with a perpendicular line detector (108) can directly acquire usable data in similar signal to noise ratio as synchrotron source. The main drawback associated with synchrotron assays available in the art are non-availability of data collection time on synchrotron sources around the world which delays report generation time for patient in practical sense. However, on the other hand, in-house SAXS machine (100) modified using the method as provided in the present application presents a more practical solution to use hair core structure analysis to interpret presence/absence of breast cancer.

Specifically, the present invention is directed to a non-invasive and patient independent or remote screening of presence of cancer by performing and analyzing small angle X-ray (SAXS) scattering intensity profile from single hair sample (106) in automated manner. The disclosed method relies on collection of SAXS data using X-rays in line collimation and scattering captured on a perpendicular line detector (108). From acquired and desmeared SAXS intensity profile, the value R' is computed which is a relationship of R, relative area under the peaks at 1.38 nm-' or 4.7 nm and 0.78 nm-1 or 8.05 nm, respectively and D, thickness of the hair calculated using laser interference or R=R2/(D−R). By analyzing clinically characterized samples, it was found that R' values are significantly lower than a threshold value for hairs from cancer positive cases, compared to those not having cancer or on oncotherapy. It has been found that this methodology can be applied for automated analysis for hair to diagnose presence/absence of cancer in sample provider.

The Applicant developed programs which automatically ascertain whether the peak profile close to 1.38 nm$^{-1}$ or 4.7 nm is substantially diminished or not relative to the peak at 0.78 nm$^{-1}$ or 8.05 nm and corrected for the thickness of the hair allows correlation with clinically confirmed cases having or lacking cancer.

A process to automatically screen for presence or absence of cancer by analyzing SAXS profile of hair is described here. The process of the invention involves:

1. Automated Loading of Hair sample (106) in the SAXS machine (100):

Hair samples (106) were aligned using a cross-talking hair holder (104) which can move up and down vertically, and a set of three pin diodes (114) which helped in automatically aligning one hair sample (106) at a time in the X-ray beam.

2. SAXS Data Collection:

Post-alignment, a SAXS data collection protocol was automatically initiated, and data was collected for ten minutes for each hair sample (106). Post-data collection, the program allowed the step 1 to occur again for the next hair in the loader, and so on.

3. SAXS Data Processing with an SAXS data processor (110):

SAXS data was corrected for beam position, and the SAXS intensity profile was analyzed by a set of programs written in our lab. The program computed a relationship, R' which arises from relative peak area under those for keratin and lipid, and corrects it for hair thickness.

There are some publications available in the art, which cite the inability of Hair SAXS to interpret breast cancer. It is highlighted that in most of the cases available in the art, the methodology of data collection has not been automated which leads to differential results. Contrarily, as presented above, the primary technical features of the present invention are: automated alignment in X-rays, automated data collection, processing and interpretation. The present invention also uses Kratky Analysis of SAXS data which amplifies signals over noise, Keratin peak as normalizing factor and relative mapping of lipid peak. Furthermore, the present invention uses hair thickness as a correcting step to finally interpret presence/absence of breast cancer in sample provider. These steps are essential for the reliable interpretation which has been provided in the present application. Further, these steps are also innovative as they have not bene reported in the technologies/methodologies forming part of state of the art.

The data of the present application was trained and tested on about 84 cancer and 93 clinically confirmed non-cancer cases. The present methodology was also able to track the recovery status of 58 out of 63 cases. Compared to other methods available in the art for screening cancer, the present method is innovative as it is non-invasive, remote and has internal normalization factors and does not rely on human interpretation of data.

EXAMPLES

The following examples are given by way of illustration of the present invention and therefore should not be construed to limit the scope of the present invention

Example 1: Flow Chart of the SAXS Data Processing Steps

The flow chart of the SAXS data processing steps and formula allows analysis of lipid to keratin architecture inside hair corrected for the thickness of hair. In FIG. 1, different steps involved in processing of desmeared SAXS data from single hair of sample provider are displayed. These computations provide a value named R' which provides a quantitative indication of non-crystalline or oriented nature of lipids in hair relative to keratin content. The protocol also corrects for thickness of hair since this technique is a transmittance methodology.

Example 2: Box Chart Representation of the Computed R' Value

Box chart representation of the computed R' value from hairs of 42, 42 and 93 cases having orthogonally confirmed profile of having breast cancer, cancers other than breast cancer (Lung cancer, pancreatic cancer, head-and-neck cancer, cervical cancer etc.) and not having any cancer, respectively is provided. This representation allows a graphical view of how the R' value is centered on lower values in cancer confirmed cases vs. those lacking similar clinical malady. Data compilation implied that using our methodology, R' values below 0.7 indicated presence of cancer, and values higher than 0.8 support absence of cancer. Of course, this value can change provided data reduction is different or arising changes from optical set-up differences or lack of thickness correction. Otherwise, these values have been internally normalized and can be considered as quantitative. The differences in observed values were statistically found to significant.

Example 3: Box Chart Representation Showing Change in R' Value

FIG. 3 illustrating the box chart representation showing change in R' value as a result of oncotherapy by following 58 of 63 breast cancer patients is presented here. This representation aided in supporting that our methodology can identify restoration of normal like profile in the hair SAXS of the patient post-therapy. The methodology tracked that with time in 58 of 63 patients (who could be tracked for samples), the lipid/keratin ratio corrected for hair thickness showed recovery of higher values. This supports that the present invention can identify recovery cases and can be used to monitor the patient status, and possibly forewarn of relapse if sample is routinely provided.

Advantages of the Invention

1. The present invention is based on usage of end user X-ray sources coupled with SAXS optics and does not require access to Synchrotron X-rays for data collection.
2. The present method involves complete automated analysis of data and does not require manual curation to interpret presence of cancer in the sample provider.
3. The present methodology provides semi-quantitative estimation of the disease state and recovery upon therapy.
4. The present methodology does not require patient presence for analysis.
5. The present method is least invasive as it requires plucked hair from scalp.
6. The present method corrects for hair thickness variation
7. The present method can identify patient recovery status, and if screened at median intervals, can even forewarn about relapse.
8. The present method is extendable to different cancers.

REFERENCES

1. Chikawa, J., Y. Mouri, et al. (2014). "A correlation of breast cancer and calcium levels in hair analyzed by X-ray fluorescence." J Xray Sci Technol 22(5): 587-603.
2. Corino, G. L. and P. W. French (2008). "Diagnosis of breast cancer by X-ray diffraction of hair." Int J Cancer 122(4): 847-856.
3. P. W. French., Dharmica A. H. Mistry, et al. (2012). "Identification of breast cancer associated lipids in scalp hair." Breast Cancer (Auckl). 06, 113-123.
4. Corino, G. L., P. W. French, et al. (2009). "Characterization of a Test for Invasive Breast Cancer Using X-ray Diffraction of Hair-Results of a Clinical Trial." Breast Cancer (Auckl) 3: 83-90.
5. P. W. French., Dharmica A. H. Mistry, (2016). "Circulating phospholipids as biomarkers of breast cancer: A review" Breast Cancer (Auckl). 10, 191-196.
6. Kajiura, Y., S. Watanabe, et al. (2006). "Structural analysis of human hair single fibres by scanning microbeam SAXS." J Struct Biol 155(3): 438-444.
7. Meyer, P., R. Goergl, et al. (2000). "Breast cancer screening using small-angle X-ray scattering analysis of human hair." J Natl Cancer Inst 92(13): 1092-1093.
8. Stephenson, J. (1999). "X-ray analysis of hair reveals breast cancer." JAMA 281(17): 1578-1579.
9. James V[1], Corino G, et al. (2005). "Early diagnosis of breast cancer by hair diffraction." Int J Cancer. 10; 114 (6):969-72.
10. James V[1], (2013). "A Review of Low Angle Fibre Diffraction in the Diagnosis of Disease". British Journal of Medicine and Medical Research, 2231-0614(3).
11. James V[1], Kirby N. (2010). "The connection between the Presence of Melanoma and changes in fibre diffraction patterns". Cancers (Basel), 1155-65(2).
12. James V[1], (2003). "False-Positive Results in studies of changes in fibre diffraction of Hair from patients with breast cancer may not be false". JNCI, 95(2), 170-171.
13. James V J, Ford J M O, Buttigieg J (2015) "Then there were none!". Integr Cancer Sci Therap. 10(2).15761

14. James V[1], et al. (1999). "Using hair to screen for breast cancer." Nature. 398, 33-34
15. James V[1], (2014). "Using Physics to Diagnose Cancer". Biophys. Rev. Lett., 09, 205

PATENTS

| | | |
|---|---|---|
| WO2000034774A1 | December 1998 | James et. al |
| WO2008000020A1 | June 2006 | Corino et. al |
| US20090299642A1 | June 2006 | French et. al |
| WO2008134800A1 | May 2007 | French et. al |
| WO2011000020A1 | June 2009 | French et. al |
| WO2010141998A1 | June 2009 | French et. al |
| WO2018096557A1 | November 2016 | Ashish et al. |

We claim:

1. An in vitro method for detecting presence of cancer, said method comprising the steps of:
   (a) obtaining a single hair sample;
   (b) emitting an x-ray beam from a source towards the hair sample;
   (c) generating a small angle X-ray scattering (SAXS) intensity profile after the x-ray beam hits the hair sample;
   (d) receiving the SAXS profile on a perpendicular line detector and obtaining SAXS data;
   (e) desmearing the SAXS data and performing Kratky Analysis;
   (f) performing relative estimation of peak area under 1.38 nm$^{-1}$ to 0.89 nm$^{-1}$ from keratin and lipid content in the hair sample to obtain R;
   (g) correcting value of R by dividing by D, wherein D is a thickness of the hair in micron;
   (h) computing R' by a formula: $10 \times R^2/(D-R)$; and
   (i) comparing the value of R' with clinically validated samples;
   wherein R' value below 0.7 is indicative of presence of cancer and R' value above 0.8 indicates absence of cancer.

2. The method as claimed in claim 1, wherein emitting the x-ray beam from the source comprises emitting the x-ray beam from a source of monodisperse X-rays.

3. The method as claimed in claim 1, wherein receiving the SAXS profile on the perpendicular line detector comprises receiving the SAXS profile on the perpendicular line detector selected from the group consisting of X-ray sensitive films, a CCD, a 1D detector, and a 2D detector.

* * * * *